(12) United States Patent
Maciejewski

(10) Patent No.: US 8,750,962 B2
(45) Date of Patent: Jun. 10, 2014

(54) MEDICAL IMAGING DEVICE

(75) Inventor: Bernd Maciejewski, Markt Erlbach (DE)

(73) Assignee: Siemens Aktiengesellschaft, München (DE)

( * ) Notice: Subject to any disclaimer, the term of this patent is extended or adjusted under 35 U.S.C. 154(b) by 0 days.

(21) Appl. No.: 13/211,421

(22) Filed: Aug. 17, 2011

(65) Prior Publication Data

US 2012/0046537 A1 Feb. 23, 2012

(30) Foreign Application Priority Data

Aug. 18, 2010 (DE) .......................... 10 2010 039 469

(51) Int. Cl.
*A61B 5/05* (2006.01)

(52) U.S. Cl.
USPC .......................................... 600/410; 156/277

(58) Field of Classification Search
USPC ............ 600/407–429; 324/309–322; 156/277
See application file for complete search history.

(56) References Cited

U.S. PATENT DOCUMENTS

| | | | | |
|---|---|---|---|---|
| 3,186,300 A | * | 6/1965 | Littmann | 359/376 |
| 4,993,790 A | * | 2/1991 | Vick | 359/20 |
| 6,346,312 B1 | * | 2/2002 | Billoni | 428/195.1 |
| 7,999,546 B2 | * | 8/2011 | Trowell et al. | 324/318 |
| 8,331,031 B2 | * | 12/2012 | Hoffman et al. | 359/621 |
| 8,379,893 B2 | * | 2/2013 | Klemenz et al. | 381/312 |
| 8,526,086 B2 | * | 9/2013 | Trantoul et al. | 359/2 |
| 2003/0169514 A1 | * | 9/2003 | Bourdelais et al. | 359/707 |
| 2004/0166258 A1 | * | 8/2004 | Mau et al. | 428/34.1 |
| 2008/0283187 A1 | * | 11/2008 | Ornetsmuller | 156/277 |
| 2009/0093705 A1 | * | 4/2009 | Vangdal | 600/410 |
| 2009/0143774 A1 | * | 6/2009 | Uzunbajakava et al. | 606/13 |
| 2009/0290733 A1 | * | 11/2009 | Klemenz et al. | 381/312 |
| 2010/0056902 A1 | * | 3/2010 | Granzer et al. | 600/415 |

FOREIGN PATENT DOCUMENTS

| | | |
|---|---|---|
| CN | 1422593 A | 6/2003 |
| CN | 101056577 A | 10/2007 |
| CN | 101069643 A | 11/2007 |
| CN | 101501520 A | 8/2009 |
| DE | 35 13919 A1 | 10/1986 |
| DE | 10 2006 021 355 A1 | 11/2007 |
| WO | WO 2005120341 A1 | 12/2005 |
| WO | WO 2006051497 A1 | 5/2006 |
| WO | WO 2010033836 A2 | 3/2010 |

\* cited by examiner

*Primary Examiner* — Sanjay Cattungal

(57) ABSTRACT

A medical imaging device having a tubular receiving region to receive a patient on a patient couch is proposed. The medical imaging device has a wall at least partially enclosing the receiving region. The medical imaging device features a film disposed on the wall at least partially enclosing the receiving region for generating at least one virtual image. The virtual image refers to a visual mapping of a light-reflecting object and/or an illuminated object.

6 Claims, 2 Drawing Sheets

MEDICAL IMAGING DEVICE

CROSS REFERENCE TO RELATED APPLICATIONS

This application claims priority of German application No. 10 2010 039 469.6 filed Aug. 18, 2010, which is incorporated by reference herein in its entirety.

FIELD OF THE INVENTION

The present invention relates to a medical imaging device having an in particular tubular receiving region to receive a patient on a patient couch, and a wall at least partially enclosing the receiving region.

BACKGROUND OF THE INVENTION

Medical imaging devices, for example magnetic resonance devices or computed tomography devices, comprise a receiving region, in particular a circular cylinder-shaped and/or tubular receiving region to receive a patient. In conventional medical imaging devices this receiving region has a maximum diameter of approx. 60 cm to 70 cm. The patient lies on a patient couch inside this receiving region for a medical examination and/or for medical imaging. The distance between the face and/or eye region of the patient and a wall of the medical imaging device enclosing the receiving region is therefore maximum 25 cm to 30 cm, which can cause many patients to experience feelings of claustrophobia and/or unease. When the medical imaging device is used to perform a measurement it is however particularly important for the patient to be as relaxed and still as possible on the patient couch inside the receiving region to prevent any negative impact on and/or falsification of a measurement result, for example due to patient movement.

A medical imaging device having a receiving region to receive a patient is known from WO 2006/051497 A1. This medical imaging device comprises a flat mirror, which is disposed inside the receiving region parallel to a couch surface of a patient couch. However this mirror must also be configured to be magnetic-resonance-compatible for deployment in a magnetic resonance device, which makes the production of the mirror expensive. Also the mirror takes up a lot of space inside the receiving region and can therefore cause the patient to be impeded and/or at least restricted inside the receiving region.

A medical imaging device is also known, wherein a simple colored adhesive strip is disposed inside the receiving region. However because of its proximity to the patient this adhesive strip can cause the patient to feel ill at ease by placing an excessive strain on the eye muscles of the patient.

SUMMARY OF THE INVENTION

The object of the present invention is in particular to provide a medical imaging device, wherein the patient feels at ease during a medical imaging examination with little outlay. The object is achieved by the features of the independent claim. Advantageous embodiments of the invention are described in the dependent claims.

The invention is based on a medical imaging device having an in particular tubular receiving region to receive a patient on a patient couch and a wall at least partially enclosing the receiving region.

It is proposed that the medical imaging device should have a film disposed on the wall at least partially enclosing the receiving region, said film generating at least one virtual image. The medical imaging device is advantageously formed by a magnetic resonance device or a computed tomography device. In this context a virtual image refers in particular to a visual mapping of a light-reflecting object and/or an illuminated object, which in contrast to a real image cannot be displayed on a screen. The light-reflecting and/or illuminated object here is disposed between a focal point of at least one lens and the at least one lens. The inventive embodiment allows a depth effect of the receiving region to be suggested to the patient inside the receiving region, in that a greater, virtual distance between the patient on the patient couch and the wall with the film disposed on it than the actual distance between the patient and the wall can be suggested to and/or simulated for said patient. For patients with a tendency to claustrophobic anxiety states in particular this can induce a feeling of well being and/or at least partially suppress any claustrophobic anxiety states as a result of a suggested and/or simulated depth effect of the film. A depth and/or thickness of film suggested to the patient is at least twenty times the structurally required depth and/or thickness of film and particularly advantageously at least thirty times the structurally required depth and/or thickness of film, so that the film produces a three-dimensional impression and/or effect for the patient. The film has a thickness of approx. 0.5 mm to 0.6 mm, the depth effect being up to 20 mm or the virtual image being disposed at a virtual distance of up to 20 mm in particular from the viewpoint of the patient or a viewer behind the surface of the film. This depth effect can be achieved particularly economically inside the receiving region by using a film. The film also allows a patient to concentrate and/or focus his/her eyes and/or attention on the film during a measurement, which can help the patient relax significantly during an imaging measurement, thereby preventing unnecessary and in particular undesirable movement of the patient.

It is also proposed that the film should comprise at least two layers, thereby allowing the depth effect or virtual image to be generated in a structurally simple and space-saving manner by means of the film. It is particularly advantageous here for the film to have at least one layer, which comprises a plurality of optical lens elements, thereby allowing a sharp, undistorted image to be generated when the film is viewed from any direction. The layer with the plurality of optical lens elements is preferably formed by a top layer, which is disposed on a side of the film facing the patient. The optical lens elements are preferably formed by convex lens elements, the diameter of the individual convex lens elements being a multiple smaller than the thickness of the film.

If the film has at least one layer, which is printed at least partially on the front, it is also possible to generate a virtual background image for the patient to look at. In this context a layer printed on the front means in particular that a surface of the layer facing the receiving region is printed with a motif, in particular a colored motif. The motifs printed on the surface of the layer are preferably disposed from the patient's viewpoint behind the layer with the optical lens elements and are mapped by these to generate the virtual image. The film preferably comprises a number of layers printed on the front. In an interaction with a top layer made up of a plurality of optical lens elements, virtual images of the different layers, in particular of the layers printed on the front, can be shown in different depth planes, thereby generating a three-dimensional effect for someone looking at the film or the virtual images. The layer with the optical lens elements can also have a printed surface, which however only supplies a two-dimensional image for the patient, which is in particular superimposed on the virtual background image. It is also conceivable for a number of films with different motifs to be available to be positioned inside the receiving region, so that the medical imaging device, in particular the film, can be tailored to an area of application of the medical imaging device.

In an advantageous development of the invention it is proposed that the film should be connected at least partially with a material fit to the wall at least partially enclosing the receiving region. It is particularly advantageous for the film to be bonded to the wall, allowing particularly fast and structurally simple fastening and/or attachment of the film to the wall of the medical imaging device to be achieved. The film therefore particularly advantageously assumes a contour of the wall at least partially enclosing the receiving region, so that any restriction of the receiving region can also be prevented. Further material fit connections that appear useful to the person skilled in the art are alternatively or additionally possible between the film and wall.

To prevent and/or suppress vigorous eye movement of the patient during an examination using the medical imaging device, the film has a width of maximum 10 cm and particularly advantageously a width of essentially 5 cm.

BRIEF DESCRIPTION OF THE DRAWINGS

Further advantages will emerge from the description of the drawings which follows. The drawings show an exemplary embodiment of the invention. The drawings, description and the claims contain numerous features in combination. The person skilled in the art will also expediently consider the features individually and combine them in useful further combinations. In the drawings:

DETAILED DESCRIPTION OF THE INVENTION

Figure 1:
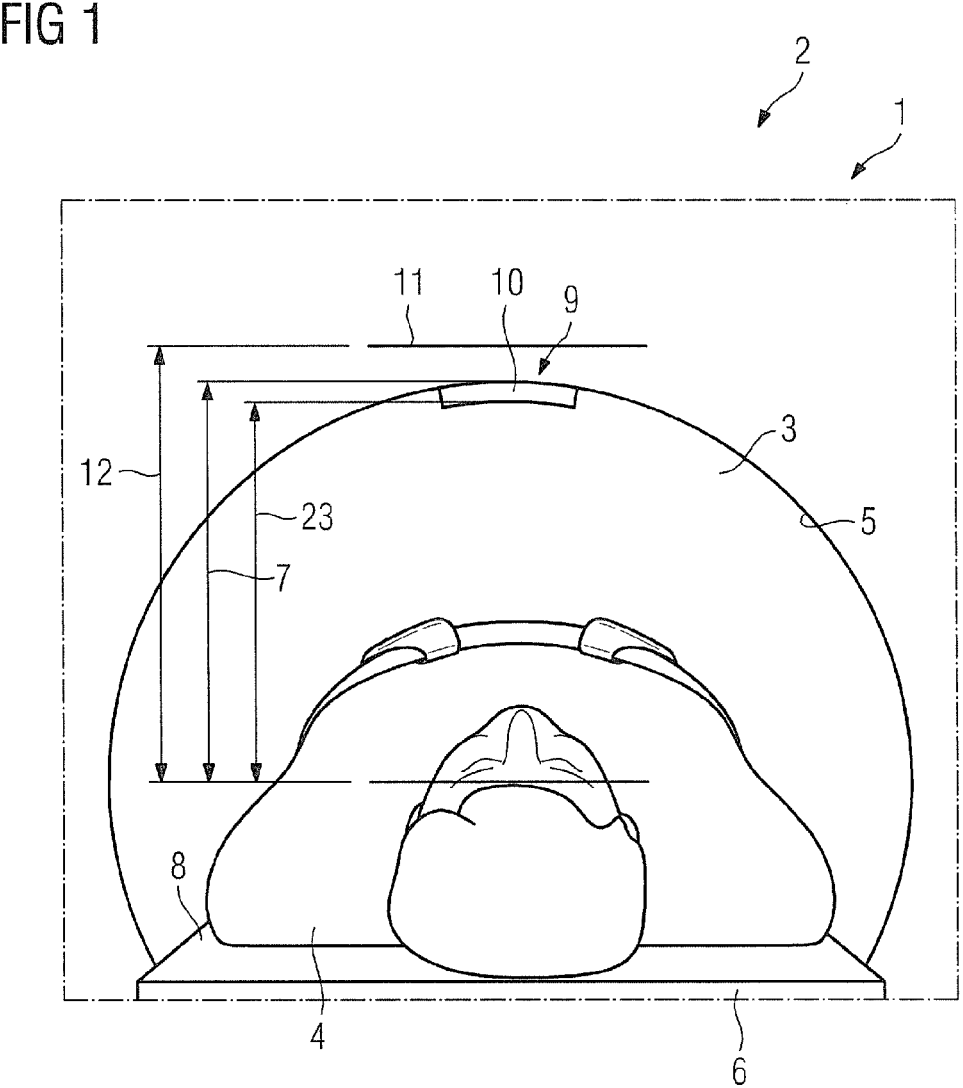
FIG. 1 shows an inventive medical imaging device.
Figure 2:
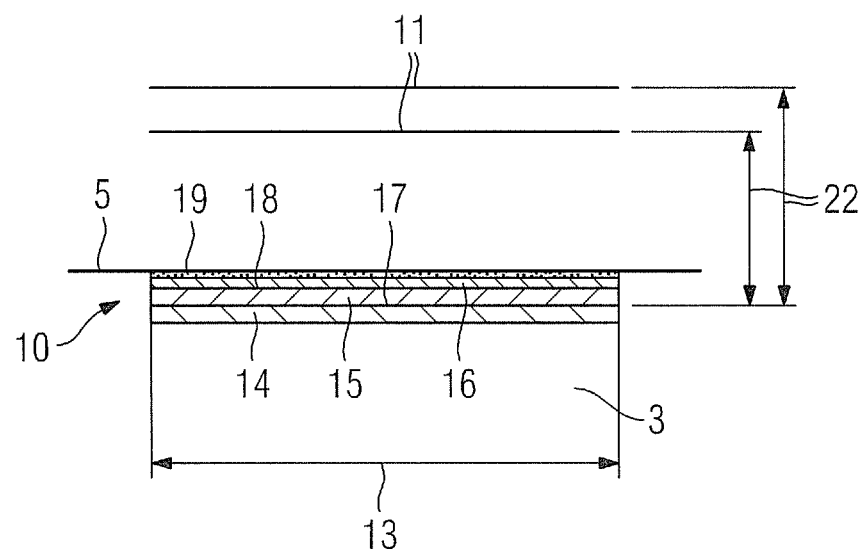
FIG. 2 shows a film of the medical imaging device with a virtual image.

FIG. 1 shows a schematic diagram of an inventive medical imaging device 1, in the present exemplary embodiment formed by a magnetic resonance device 2. The magnetic resonance device 2 comprises a receiving region 3 to receive a patient 4. The receiving region 3 is tubular, in particular circular cylinder-shaped, and enclosed by a wall 5 of the magnetic resonance device 2. The wall 5 of the magnetic resonance device 2 here is formed by a housing shell of the magnetic resonance device 2. In an alternative embodiment of the invention the medical imaging device 1 can also be formed by a computed tomography device and/or further medical imaging device, which appear useful to the person skilled in the art, having an in particular tubular receiving region 3 to receive the patient 4. A tubular receiving region 3 can also have a D-shaped cross section. The receiving region 3 can also be configured as C-shaped.

For an imaging magnetic resonance examination the patient 4 is positioned on a patient couch 6 and introduced lying on this into the receiving region 3. With the patient 4 lying on the patient couch 6 in a normal lying position the distance 7 for example between the eye region of the patient 4 and a region 9 of the wall 5 opposite and/or facing the couch surface 8 of the patient couch 6 is approx. 20 cm to 30 cm. A film 10 is disposed on this region 9 of the wall 5, generating at least one virtual image 11. The film 10 is connected to the region 9 of the wall 5 with a material fit, being bonded in particular to the region 9 of the wall 5 by means of an adhesive layer 9 of the film 10. The virtual image 11 allows a depth effect and/or a three-dimensional effect of the film 10 to be suggested to a patient 4 inside the receiving region 3, in that an actual distance 23 between the eye region of the patient 4 and a surface of the film 10 is smaller than a distance 12 between the eye region of the patient 4 and the at least one virtual image 11.

The film 10 is also disposed on the wall 5 along an essentially entire length of the receiving region 3 or along an essentially entire length of the wall 5 enclosing the receiving region 3. The film 10 has a width 13, which is aligned essentially perpendicular to the length of the film 10. The width 13 of the film 10 is maximum 10 cm and particularly advantageously essentially 5 cm, so that a patient 4 can remain still, in particular without head movements, and relaxed when looking at the film 10 during a magnetic resonance measurement and the effect of the film 10 is to induce relaxation in the patient 4, thereby preventing major eye movement at least to some degree when looking at the film 10. To this end the film 10 is disposed on the wall 5 in such a manner that the field of vision of the patient 4 is directed directly onto the film 10 in a preferred position on the patient couch 6, when the patient 4 is lying on his/her back on the patient couch 6.

In order to generate the virtual image 11 or to generate the depth effect and/or three-dimensional effect, the film 10 has a number of layers 14, 15, 16. A top layer 14, which faces the receiving region 3, has a plurality of optical lens elements, which are configured in an essentially identical manner. The optical lens elements are formed by convex lens elements and are disposed directly adjacent to one another within the top layer 14.

The film 10 also has a number of layers 15, 16, which feature a printed surface 17, 18. These layers 15, 16 are disposed between the top layer 14 and the adhesive layer 19 for bonding to the wall 5. The printed surfaces 17, 18 here are formed by a front printed surface 17, 18, the surfaces 17, 18 printed on the front facing away from the adhesive layer 19 and facing the top layer 14 with the plurality of optical lens elements and the receiving region 3. The individual layers 14, 15, 16 with the surfaces 17, 18 printed on the front are also disposed at different distances from the top layer 14 with the optical lens elements. The distance to the individual layers 15, 16 here is less than or equal to a focal length of the convex lens elements, so that virtual images 11 are formed by the mapping of motifs printed on the surfaces 17, 18. Alternatively the film 10 can have further layers that appear useful to the person skilled in the art, as required to generate a depth effect and/or the three-dimensional effect of the film 10. The layer 14 with the optical lens elements can also have a printed surface, said printed surface appearing to the patient 4 as a two-dimensional image, which is superimposed on the virtual image 11.

The top layer 14 with the optical lens elements and different actual distances between the individual layers 15, 16 with the printed surfaces 17, 18 and the top layer 14 mean that when a person looks at the film 10, a depth effect and/or the three-dimensional effect is suggested, in that a virtual image 11 is generated for each of the layers 15, 16 with a printed surface 17, 18. These different, virtual images 11 are each at a different distance 22 from the top layer 14 of the film 10. As an alternative to the present exemplary embodiment the individual layers 15, 16 with the printed surfaces 17, 18 can be at least two to five intermediate layers from the top layer 14 for example.

The film 10 is formed from a polypropylene material, in particular from a recycled polypropylene material, so that after use it can be disposed of in a particularly simple and environmentally friendly manner. It is also possible to produce a film 10 configured in this manner with low production costs and little production outlay. In one alternative embodiment of the film 10 it can also be formed by further materials that appear useful to the person skilled in the art. The film 10 has for example a thickness of approx. 0.5 mm to 0.6 mm and a virtual distance 22 between the virtual images 11 generated by the film 10 and the top layer 14 of up to 20 mm, so that an increase in the distance 7 between the patient 4 and the wall 5 enclosing the receiving region 3 is suggested to and/or simulated for the patient 4.

The invention claimed is:

1. A medical imaging device, comprising:
   a patient couch;
   a tubular receiving region for receiving the patient on the patient couch;
   a wall at least partially enclosing the tubular receiving region; and
   a film disposed on the wall for generating a virtual image,
   wherein the film comprises at least two layers comprising
      a top layer having a plurality of optical lens elements and
      a layer disposed behind the top layer,
   wherein at least part of surface of the layer disposed behind the top layer is printed with motif,
   wherein the layer disposed behind the top layer is disposed at a distance from the top layer that is less than or equal to a focal length of the optical lens elements, and
   wherein the virtual image is generated by mapping the motif.

2. The medical imaging device as claimed in claim 1, wherein the film is connected at least partially with a material fit to the wall.

3. The medical imaging device as claimed in claim 1, wherein the film has a width of maximum 10 cm.

4. The medical imaging device as claimed in claim 1, wherein the film has a width of essentially 5 cm.

5. The medical imaging device as claimed in claim 1, wherein the virtual image comprises a visual mapping of a light-reflecting object and/or an illuminated object.

6. The medical imaging device as claimed in claim 1, wherein the motif is a colored motif.

* * * * *